United States Patent [19]

Mungia, Sr.

[11] Plant 4,876

[45] Aug. 17, 1982

[54] ROSE PLANT

[76] Inventor: Fred A. Mungia, Sr., P.O. Box 338, McFarland, Calif. 93250

[21] Appl. No.: 213,910

[22] Filed: Dec. 8, 1980

[51] Int. Cl.[3] ..... A01H 5/00

[52] U.S. Cl. ..... Plt./6

[58] Field of Search ..... Plt./6

*Primary Examiner*—Robert E. Bagwill

[57] ABSTRACT

A new and distinct variety of rose plant of the climbing hybrid tea class, a sport of the unpatented rose variety known as Dame de Coeur, characterized by a very vigorous growing bush producing dark red flowers of good substance.

2 Drawing Figures

1

The present invention relates to a new and distinct variety of rose plant of the climbing hybrid tea class, which originated as a sport of the variety, "Dame de Coeur," a nonpatented variety.

The new variety was discovered by me at my nursery in McFarland, Calif., in a cultivated area. My attention was drawn to a plant that was presumed to be the variety, "Dame de Coeur," but which exhibited definite climbing characteristics in that it produced canes which were 8 to 10 feet in length. This new variety has been asexually reproduced by budding, under my supervision at McFarland, Calif. Observations of the above asexual reproductions of the new variety have shown that the climbing habit comes true to form and is transmissible through succeeding asexual propagations.

This new variety is distinguished from its parent only by its climbing habit of growth and is classified as a climbing hybird tea rose.

Among the novel characteristics possessed by this rose which distinguishes it from all other varieties of which I am aware are:

1. The plant is everblooming and produces 3½ to 4 inch flowers that last well. Flowers appear in clusters and one to a stem at times on the same plant.
2. The plant is well branched, vigorous and free standing with upright spreading habit from 8 to 10 feet tall in length.
3. Flowers have an old rose fragrance.
4. A general color tonality of the flowers corresponding to deep crimson lightly overcast with deep cherry red and the flowers are long lasting and unfading.
5. The plant is very hardy and disease resistant.

The accompanying drawing shows a specimen plant of the new variety which is illustrative of the typical climbing habit of growth and flower color in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "53A" is plate 53A of the Royal Horticultural Society Color Chart.

The following observations are made of specimens grown outdoors at Kern County, Calif., during the month of October.

2

FLOWER

Blooming habit: Continuous.

A. Bud:
- (1) *Size.*—Medium.
- (2) *Form.*—Globular.
- (3) *Color.*—When sepals first divide: near to RHS 46A with dark streaking where exposed to light. When petals begin to unfurl: near to but darker than 46A with dark velvet overtones. When half blown: inside of petals —color changes very little as flower opens, near RHS 46A. Reverse side of petal: near RHS 53A.
- (4) *Sepals.*—Long and thin extending beyond tip of bud.
- (5) *Peduncle.*—Length 2½ to 3 inches. Aspect — smooth. Strength — heavy. Color — RHS 139C with slight purple cast where exposed to light.

B. Bloom:
- (1) *Size.*—Average size when fully expanded: 3½ to 4 inches.
- (2) *Borne.*—Singly and several together on short branching canes.
- (3) *Form.*—Cupped, opens somewhat flat with ruffled petals with center of flower quartering producing a quilling effect.
- (4) *Petalage.*—44.
- (5) *Color.*—During first two days, center of flower — slightly darker than 46A with black velvet cast. Inside of petals 46A to 46B. Reverse of petals — near to RHS 53B.
- (6) *Color change.*—General tonality from a distance — near RHS 46A with more scarlet to cherry red tone than 46B. Color is very stable and uniform and shows no bluing as flowers age.

C. Petals:
- (1) *Texture.*—Thick.
- (2) *Appearance.*—Inside — velvety; outside — satiny.
- (3) *Form.*—Ovoid.
- (4) *Arrangement.*—Imbricated (regularly arranged shingle-like).
- (5) *Petaloids in center.*—Few.
- (6) *Persistence.*—Drop off clean.
- (7) *Fragrance.*—Slight. Old rose.
- (8) *Lasting quality.*—Good on plant and as cut flower.

REPRODUCTIVE ORGANS

A. Stamens, anthers: Medium size, many arranged around styles.
(1) *Color.*—Light orange yellow 13C.
B. Pollen:
*Color.*—17D.
C. Styles: Bunches, uneven length.
D. Stigmas:
*Color.*—Orange yellow — 16A.
E. Hips: None observed.

PLANT

A. Form: Climber.
B. Growth: Very vigorous and upright.
*Height attained.*—8 to 10 ft. high.
C. Foliage: Compound of 5 to 7 leaflets.
(1) *Size.*—Large.
(2) *Quantity.*—Abundant.
(3) *Color.*—New foliage: upper side — 137A; with leathery glossy foliage with light purple overcast under side — dull near 147C. Old foliage: upper side — RHS 137A; under side — 147C.
(4) *Shape.*—Pointed.
(5) *Texture.*—Upper side — leathery with glossy finish. Under side — rough.
(6) *Edge.*—Almost smooth.
(7) *Serration.*—Very small on tip.

(8) *Leaf stem.*—Color — RHS 139C with bronze cast; under side — 139C.
(9) Stipules.—Thin and pointed; no bearding.
D. Wood
(1) *New wood.*—Color — 182A with green undercast. Bark — smooth.
(2) *Old wood.*—Color — 137B. Bark — smooth.
E. Thorns:
(1) *Thorns.*—Quantity: on main stalks from base — ordinary; on laterals from stalk — few. Form: flat base. Length: medium. Color when young — 178C. Position: regular.
(2) *Prickles.*—Quantity: on main stalks — few; on laterals — none.
F. Plant's disease resistance:
*Mildew.*—Very good.
*Blackspot.*—Very good.
*Rust.*—None observed.
G. Winter hardiness: Good.

I claim:

1. A new and distinct variety of rose plant of the climbing hybrid tea class, substantially as herein shown and described, characterized particularly as to novelty by its general similarity to its parent variety, "Dame de Coeur", but different therefrom by its pronounced climbing growth habit.

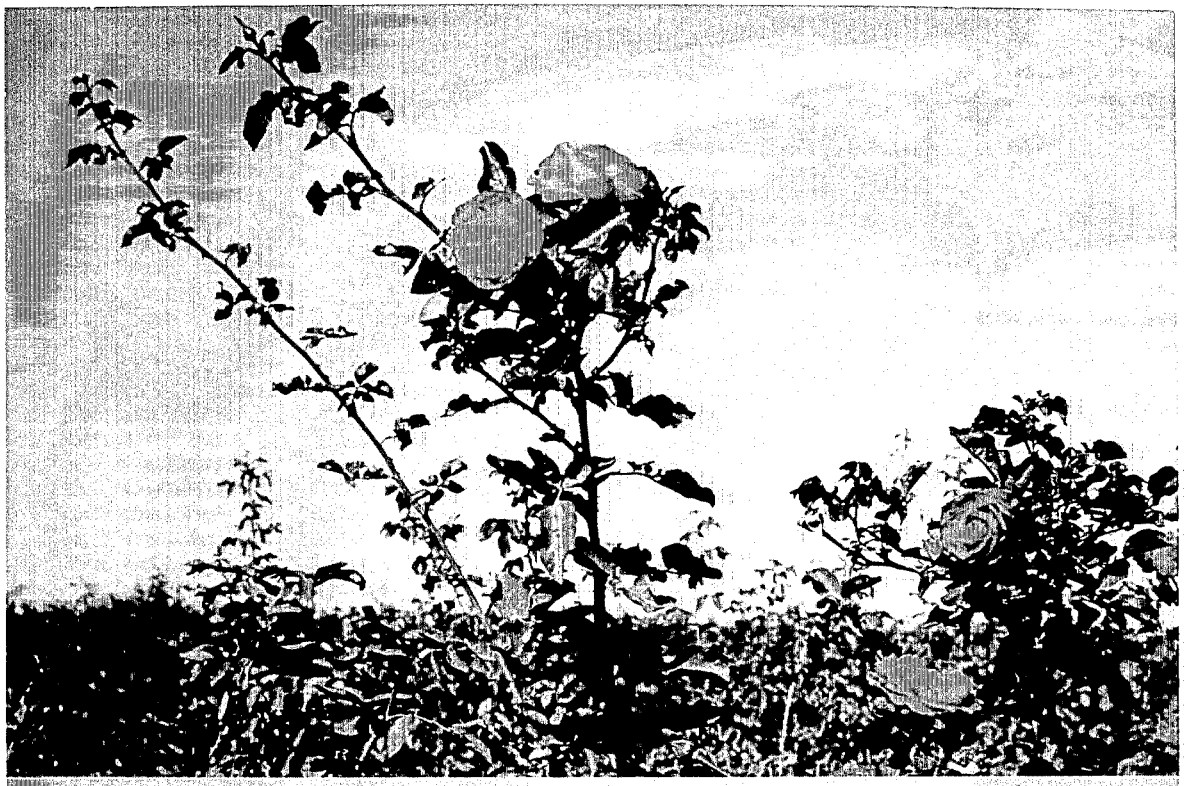
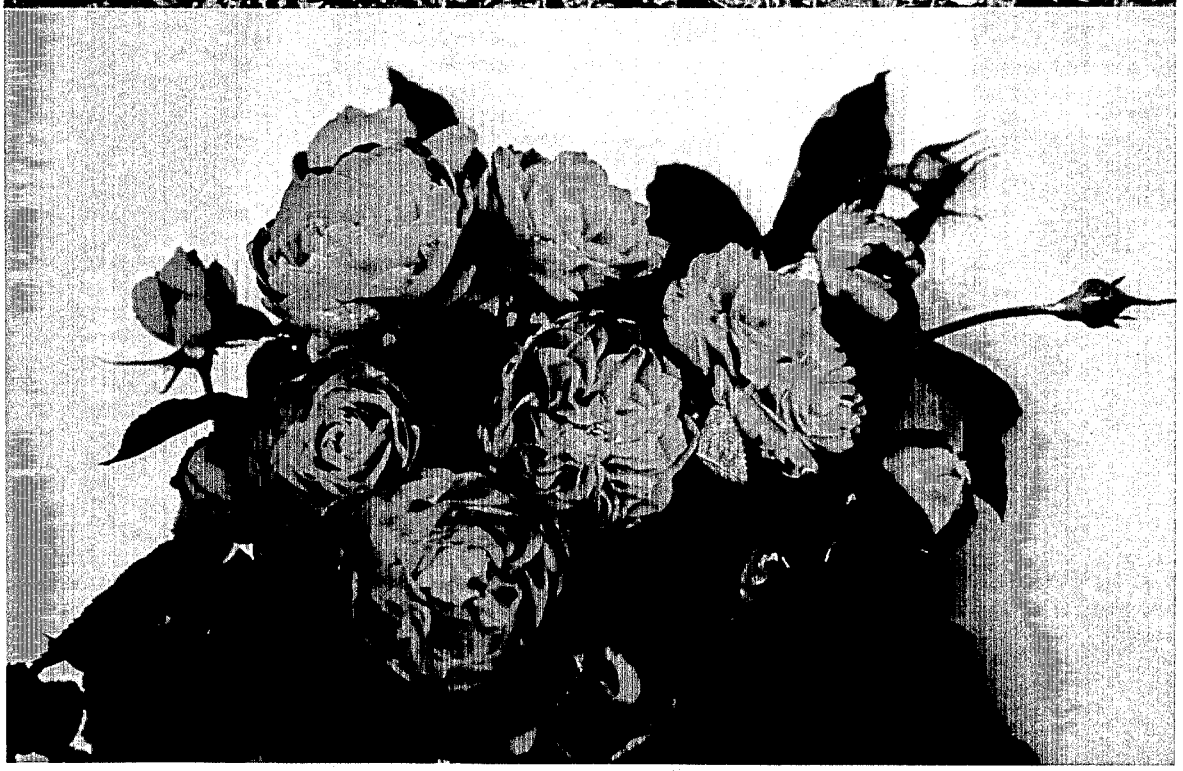

* * * * *